(12) United States Patent
Chen

(10) Patent No.: US 8,157,567 B2
(45) Date of Patent: Apr. 17, 2012

(54) ENDOSCOPE SIMULATION APPARATUS AND SYSTEM AND METHOD USING THE SAME TO PERFORM SIMULATION

(76) Inventor: Weijian Chen, Guangzhou (CN)

( * ) Notice: Subject to any disclaimer, the term of this patent is extended or adjusted under 35 U.S.C. 154(b) by 150 days.

(21) Appl. No.: 12/829,944

(22) Filed: Jul. 2, 2010

(65) Prior Publication Data
US 2010/0273134 A1 Oct. 28, 2010

Related U.S. Application Data

(63) Continuation of application No. PCT/CN2008/000880, filed on Apr. 30, 2008.

(30) Foreign Application Priority Data

Jan. 7, 2008 (CN) ...................... 2008 2 0042403 U

(51) Int. Cl.
*G09B 23/28* (2006.01)
(52) U.S. Cl. ...................................................... 434/262
(58) Field of Classification Search ............. 434/55, 434/57, 58, 61, 62, 63, 67, 262, 272
See application file for complete search history.

(56) References Cited

U.S. PATENT DOCUMENTS

| | | | |
|---|---|---|---|
| 5,722,836 A | 3/1998 | Younker | |
| 5,800,177 A | 9/1998 | Gillio | |
| 6,024,576 A * | 2/2000 | Bevirt et al. | 434/262 |
| 6,113,395 A * | 9/2000 | Hon | 434/262 |
| 6,470,302 B1 * | 10/2002 | Cunningham et al. | 703/7 |
| 6,902,405 B2 * | 6/2005 | Irion et al. | 434/272 |
| 7,594,815 B2 * | 9/2009 | Toly | 434/262 |
| 2005/0142525 A1* | 6/2005 | Cotin et al. | 434/262 |
| 2006/0211917 A1* | 9/2006 | Ikemoto et al. | 600/118 |

FOREIGN PATENT DOCUMENTS

| DE | 10304736 B3 | 9/2004 |
|---|---|---|
| EP | 1722346 A1 | 11/2006 |

* cited by examiner

*Primary Examiner* — Kurt Fernstrom
(74) *Attorney, Agent, or Firm* — Muncy, Geissler, Olds & Lowe, PLLC

(57) ABSTRACT

An endoscope simulation apparatus aims to offer improved simulation, a simpler structure and can be fabricated at lower costs. The endoscope simulation apparatus comprises a bracing rack, a spheroid and a controlling bar. The spheroid is held in the bracing rack and turnable freely. The controlling bar is slidable relative to the spheroid in a passage running through the center of the spheroid to control rotation of the spheroid. The bracing rack has an inner side spaced from the spheroid to hold at least two direction sensors. The controlling bar has a depth sensor. The controlling bar is a simulated endoscope and also is insertable and retractable. The invention can be turned at a greater angle and provide improved simulation through the turnable spheroid. Through the direction sensors and depth sensor that are linked to a computer, the turning angle and insertion depth of the simulated endoscope can be measured.

20 Claims, 12 Drawing Sheets

ENDOSCOPE SIMULATION APPARATUS AND SYSTEM AND METHOD USING THE SAME TO PERFORM SIMULATION

This application is a continuation of PCT from PCT Patent Application No. PCT/CN2008/000880 filed on Apr. 30, 2008, entitled "AN ENDOSCOPE SIMULATION INSTALLMENT AND ITS SYSTEM AND ITS SIMULATION METHOD", the entire contents of which are hereby incorporated by reference.

FIELD OF THE INVENTION

The present invention relates to a simulation practice equipment to simulate surgical instruments and particularly to an endoscope simulation apparatus that is simply structured and provides improved simulation.

BACKGROUND OF THE INVENTION

Endoscope is a commonly used instrument in minimally invasive surgery and has been widely used in various types of surgical operations. It takes a long training for a surgeon using the endoscope proficiently. The training generally needs to perform on living bodies or corpse samples. Such a training opportunity usually is rare for students studied in medical schools or interns. Therefore, it generally takes a very long time to verse in the skill. In order to overcome such a problem of lack of practical training and operation opportunities, many analog simulation systems have been developed. With advanced development of computer technology, such simulation systems now can combine with simulation image software to achieve desirable simulation effect. However, the simulation equipment for endoscope operation at present still cannot achieve real simulation effect. Its main drawback results from adopting a gear structure which limits rotation angle thus free rotation angle is small. Moreover, the gear structure is complex and easily malfunctions, and is costly to fabricate, repair and maintain. Furthermore, the conventional structure merely simulates rotation and insertion/drawing slide movements of the endoscope, and cannot simulate the conditions of encountering damping and obstacles while the endoscope is inside a human body. As a result, the conventional analog simulation apparatus can accomplish merely operational practice, but cannot provide tactile feeling, or called hand-touch feel that is the most important skill during surgical operation for doctors. Hence even after using the conventional simulation apparatus for practice for a long time, a lengthy practical operation still is needed to develop the skill required.

SUMMARY OF THE INVENTION

The primary object of the present invention is to overcome the deficiency of the conventional technique by providing an endoscope simulation apparatus that offers improved simulation, is simply structured and can be fabricated at a lower cost.

Another object of the invention is to provide a high quality simulation apparatus to achieve controllable simulation or feedback simulation.

The endoscope simulation apparatus according to the invention includes a bracing rack, a spheroid and a controlling bar. The spheroid is held in the bracing rack and turnable freely. The controlling bar slidably runs through a passage formed in the center of the spheroid to control rotation of the spheroid. The bracing rack has an inner side spaced from the spheroid to hold at least two direction sensors therebetween. The controlling bar has a depth sensor located thereon. The controlling bar is a simulated endoscope to control rotation of the spheroid and also is movable for insertion and drawing. The invention adopts the turnable spheroid structure and can be turned at a greater angle and provide improved simulation over the conventional gear structure. Through the direction sensors and depth sensor that are linked to a computer, the rotational angle and inserted depth of the simulated endoscope can be measured. The invention is constructed in a simple structure with fewer elements, thus the cost is lower. It also employs a common interface to link the computers. The simulation system can be configured by users by merely installing corresponding simulation software. Students or interns require only a computer installed with analog software, then can do exercise, even at home. It is desirable for teaching and training.

To achieve sliding agility and freedom of the spheroid, the apparatus of the invention provides at least two rotational bracing decks between the inner side of the bracing rack and the spheroid. Each rotational bracing deck has rolling balls on the top to incorporate with sliding of the spheroid. In general, three rotational bracing decks are provided between the inner side of the bracing rack and the spheroid. The three rotational bracing decks are located on planes running through the center of the spheroid, and spaced evenly from each other relative to the center of the spheroid. Another alternative is to provide four rotational bracing decks between the inner side of the bracing rack and the spheroid that are spaced from each other in a regular tetrahedron. The regular tetrahedron has a gravity center coincided with the center of the spheroid. Because of such an even distribution structure of the rotational bracing decks, the stability of the apparatus improves. It also provides sufficient moving space for the controlling bar, such that the free rotation angle is not limited, thus also improves simulation effect.

The invention also provides a turning angle sensor between the passage and the controlling bar to measure the rotational angle of the controlling bar relative to the spheroid. The turning angle sensor can measure the turning angles while the controlling bar is in the simulation process, and is adaptable to some special types of endoscopes.

The sensors mentioned above may adopt optical sensors or mechanical sensors. The passage in the spheroid can be a non-closed or closed structure. For the non-closed structure, the depth sensor is held inside the spheroid between the passage and the controlling bar. Such a structure is more stable and precise, and can select optical sensors or mechanical sensors. For the closed structure, the depth sensor can be located at one end of the passage facing a distal end of the controlling bar. Such a structure is more compact, but can use only the non-contact optical sensors.

The direction sensor can be an optical sensor or mechanical sensor according to actual requirement. In order not to hinder rotation or constrain the rotational angle or range of the controlling bar, the direction sensor generally is installed adjacent to the rotational bracing deck, preferably at the top portion of the rotational bracing deck.

The present invention further provides a damper means between the bracing rack and the spheroid, or between the spheroid and the controlling bar, or both. The damper means can really simulates that the endoscope encounters resistance or is obstructed by tissue inside a human body without further insertion or rotation. The damper means has a manual regulator or a feedback automatic regulator, or both manual and feedback automatic regulators. The manual regulator allows users to adjust resistance of rotation and insertion according to actual requirements. The feedback automatic regulator is linked to a computer and automatically adjusts the resistance and restricts the position of rotation and insertion according to human body structure in the analog software, thereby a high quality simulation can be accomplished. By installing the damper means, simulation of real tactile feeling can be realized in operating endoscope to get real simulation effect. This effect can even be further enhanced by inputting patients' data pending to surgical operation to the computer to practice simulated surgical operation.

In order not to hinder rotation of the controlling bar and constrain rotational angle or range thereof, like the direction sensor, the damper means also is installed adjacent to the rotational bracing deck, preferably on the top portion of the rotational bracing deck.

The cross section of the controlling bar and the passage are formed at a non-circular structure so that the controlling bar can be served as a rotational shaft to control rotation of the spheroid to achieve rotation simulation of the endoscope merely through the direction sensors. The cross section of the controlling bar and passage generally are in a regular polygon, preferably a regular hexagon.

The controlling bar also has a distal end with a simulated endoscope handle and a control button to provide real handling feel or operation of the endoscope. Different types of endoscope handles can be changed to perform simulation practices of different types of endoscopes or endoscope-like surgical instruments, such as electrotomes of minimally invasive surgery and electric forceps. The turning angle sensor can measure the rotational angle of these instruments and transmit to the computer to perform analog.

The aforesaid sensors and damper means have data lines with signals thereof to be integrated and analyzed through a serial port, and transmitted to the computer through a standard interface to implement control and operation of the surgical simulation software easier.

Based on the endoscope simulation apparatus previously discussed, the invention further provides an endoscope simulation system which includes a computer, simulation software installed in the computer and an endoscope simulation apparatus. The computer and endoscope simulation apparatus are connected through a data line. As previously discussed, the endoscope simulation apparatus also includes a bracing rack, a spheroid and a controlling bar. The spheroid is held in the bracing rack and turnable freely. The controlling bar is slidable relative to the spheroid and installed in a passage running through the center of the spheroid to control rotation of the spheroid. The bracing rack has an inner side spaced from the spheroid to hold at least two direction sensors therebetween. The controlling bar has a depth sensor located thereon. The simulation software establishes a human body internal space database and a human body internal image database. The human body internal space database and human body internal image database are used to build a virtual human body internal structure in the computer.

When the damper means is installed between the bracing rack and the spheroid, or between the spheroid and the controlling bar, or between both of them, the human body internal space database also has a built-in damping database which records resistance coefficient of movement of the endoscope in the human body internal structure and impenetrable locations.

Based on the system set forth above, the invention also provides a simulation method comprising the following steps:

1. Computer establishes a human body internal virtual model based on the human body internal space database built by the simulation software and incorporates with the human body internal image database to set up a human body internal virtual scene displayed through a computer display device;

2. initialize the location of a virtual endoscope and display the location of the virtual endoscope in the virtual scene through the display device;

3. turn the spheroid through the controlling bar or insert and withdraw the controlling bar, and the direction sensors or depth sensor sends data of rotational spatial angles and insertion/withdrawing depths through a data line to the computer;

4. simulation software accumulates the data of the rotational spatial angles and insertion/withdrawing depths with the location of the virtual endoscope and displays the location of the virtual endoscope in the virtual scene after rotated through the display device; and 5. the direction sensors, depth sensor, simulation software and computer repeat steps 3 and 4 at a constant frequency, and the display device continuously displays different locations of the virtual endoscope in the virtual scene to form continuous dynamic images.

The method further includes the following steps:

6. the controlling bar is served as a shaft to turn the spheroid, and the direction sensors or turning angle sensor sends angular data of the rotation of the spheroid via the data line to the computer;

7. the simulation software accumulates the angular data with the angle of the virtual endoscope, and displays the location of the virtual endoscope in the virtual scene after rotated through the display device; and 8. the direction sensors, angle sensor, simulation software and computer repeat steps 7 and 8 at a constant frequency, and the display device continuously displays different angles of the virtual endoscope in the virtual scene to form continuous dynamic images.

When the endoscope simulation apparatus also is equipped with a feedback automatic adjustment damper means, additional steps are included as follow:

9. the simulation software obtains rotation and insertion/withdrawing damping coefficients of the virtual endoscope from the damping database based on the location of the virtual endoscope in the virtual scene, and sends to the feedback automatic adjustment damper means; and 10. the feedback automatic adjustment damper means automatically adjusts resistance of rotation and insertion/withdrawing of the spheroid and the controlling bar based on the damping coefficients.

The feedback automatic adjustment damper means can simulate resistance received by the endoscope moving and turning in a human body to provide a real hand-touch feel of using the endoscope.

The invention provides improved simulation, a simpler structure, rationalized design, higher stability, easy use, lower cost and can be fabricated in a mass production, and is suitable to teaching, learning and practice to simulate real situations to get surgical tactile feel. It even can be used for surgical rehearsal practice. The invention further is adaptable to endoscope-like equipment, thus provides diversified applications. Compared with the conventional techniques, the invention provides a higher level of reality simulation, and greater adaptability and usability, and offers a significant aid for surgeons to verse in skills. It provides a great improvement over the conventional techniques.

The foregoing, as well as additional objects, features and advantages of the invention will be more readily apparent

DETAILED DESCRIPTION OF THE PREFERRED EMBODIMENTS

Figure 1:
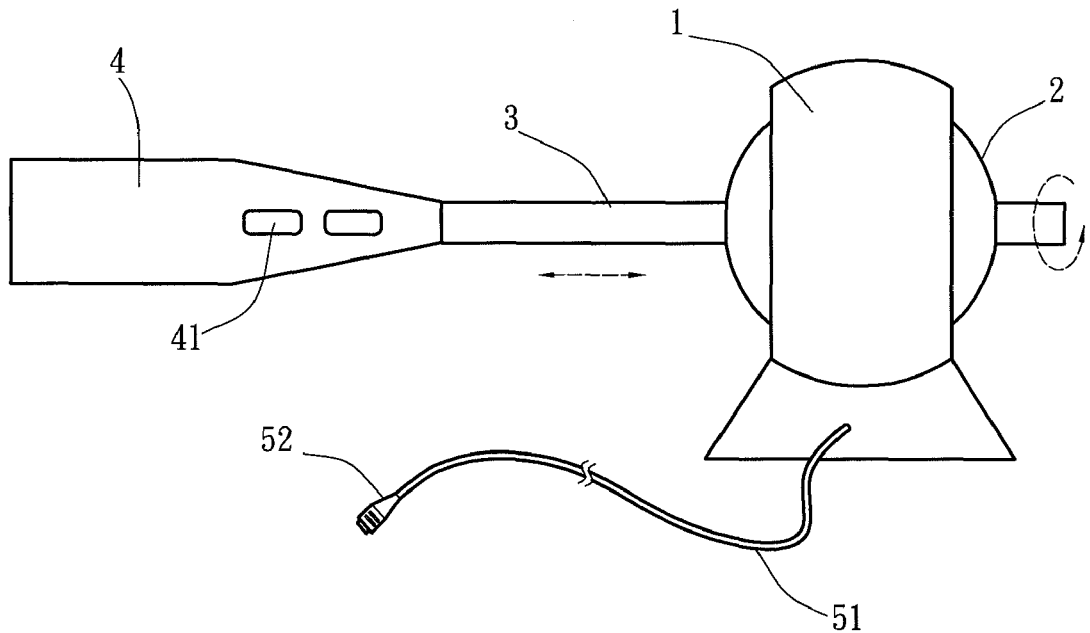
FIG. 1 is a schematic view of the structure of the first embodiment of the invention.

Embodiment 1:

The endoscope simulation apparatus according to the invention, referring to FIG. 1, includes a bracing rack 1, a spheroid 2 and a controlling bar 3. The spheroid 2 is turnable freely in the bracing rack 1. The controlling bar 3 is slidable relative to the spheroid 2 and installed in a passage running through the center of the spheroid 2 as marked by an arrow in the drawing. The bracing rack 1 is an open type. The controlling bar 3 controls the spheroid 2 to rotate in the bracing rack 1, and has one end fastened to a handle 4 to facilitate user grasping. The handle 4 is a simulated handle of an endoscope and has a button 41 located thereon. The handle 4 and the controlling bar 3 adopt a structure that can be assembled and disassembled easily so that different types of the handles 4 can be changed to simulate different types of endoscopes, or even other handles of surgical instruments to facilitate practice of other endoscope-like surgical equipment, such as electric shears of minimally invasive surgery, electric surgical scalpels and the like. The apparatus is connected to a computer through an electric cable 51 and a common interface 52 at a distal end thereof, such as USB. The computer has corresponding simulation software installed therein to show virtual human body internal structure to provide simulation practice for the endoscope.

Figure 2:
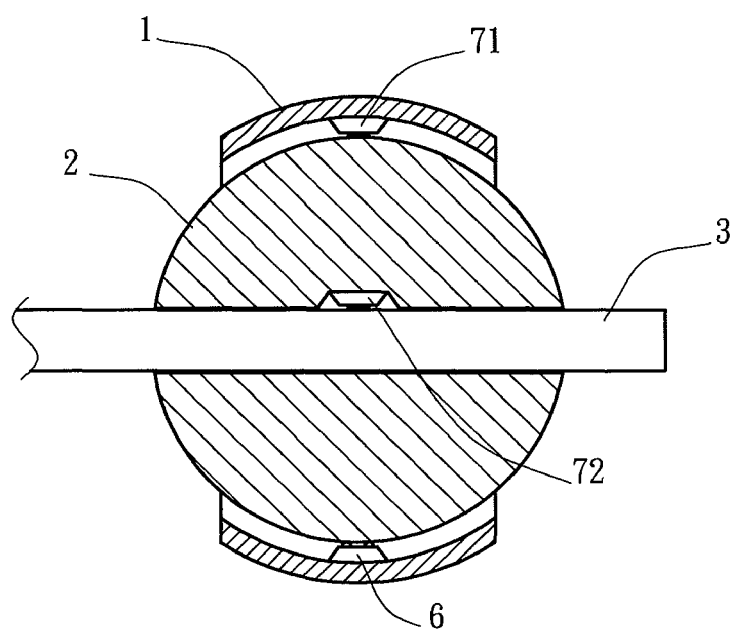
FIG. 2 is a longitudinal cross section of the main body according to FIG. 1.
Figure 3A:
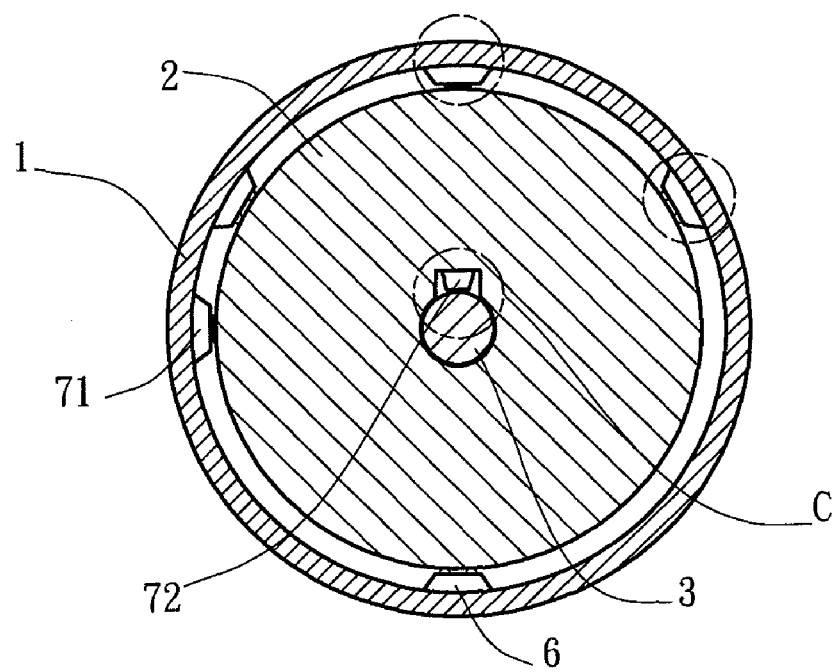
FIG. 3A is a transverse cross section of the main body according to FIG. 1.
Figure 3B:
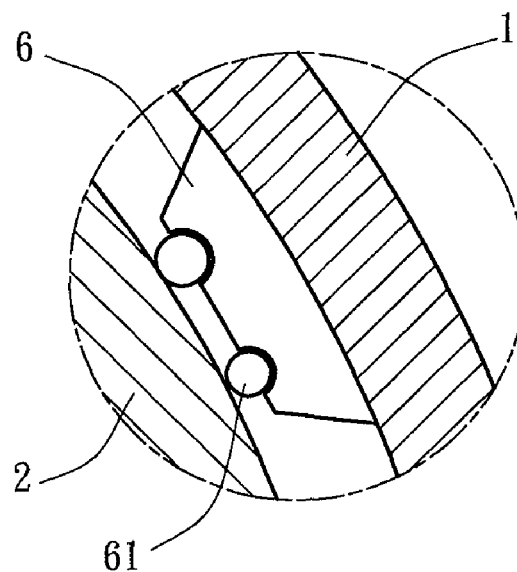
FIG. 3B is an enlarged view in FIG. 3A.
Figure 3C:
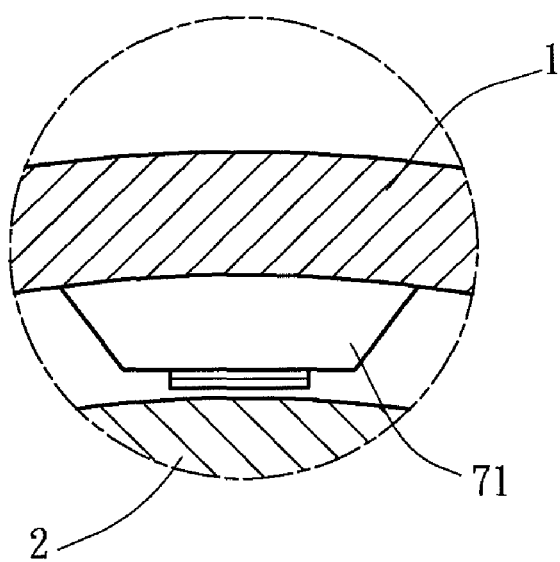
FIG. 3C is an enlarged view in FIG. 3A.
Figure 3D:
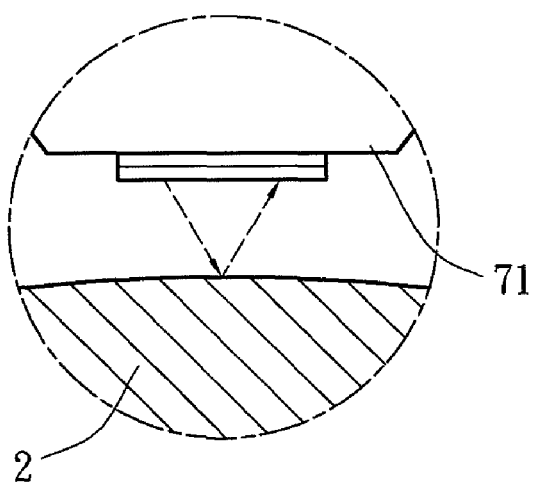
FIG. 3D is a schematic view of operation principle of sensors.
Figure 3E:
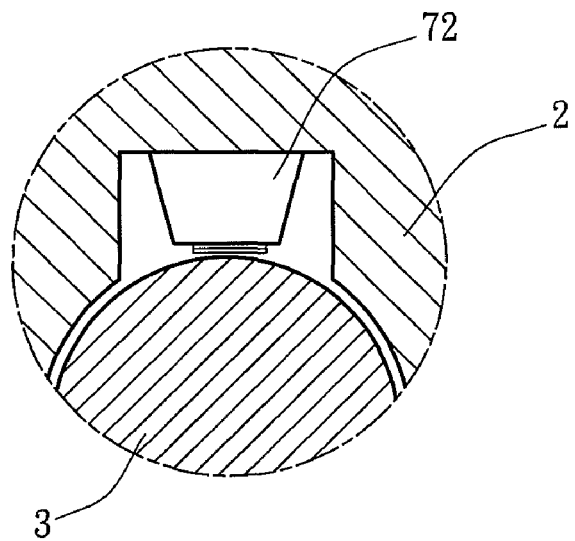
FIG. 3E is an enlarged view in FIG. 3A.

Also referring to FIGS. 2 and 3A, there are three rotational bracing decks 6 located between an inner side of the bracing rack 1 and the spheroid 2. The three rotational bracing decks 6 are located respectively on a plane running through the center of the spheroid 2, and are spaced evenly from one another at 270 degrees on the inner side of the bracing rack 1. Each rotational bracing deck 6 has rolling balls 61 on the top slidably incorporated with the spheroid 2 as shown in FIG. 3B. Such the rolling balls aims to enhance mobility of the spheroid 2 during sliding. There are two direction sensors 71 located between the inner side of the bracing rack 1 and the spheroid 2, and there is a depth sensor 72 located between the interior of the spheroid 2, passage and controlling bar 3 as shown in FIGS. 3C and 3E. The two direction sensors 71 aim to measure direction alterations of the spheroid 2 rotating relative to the bracing rack 1. The depth sensor 72 aims to measure insertion and withdrawing depth of the controlling bar 3 in the passage of the spheroid 2. The measured data of the aforesaid movements are recorded in the computer as parameter input of the simulation software to show movements of the endoscope in the virtual human body internal structure. Refer to FIG. 3D for operation principle of the sensors. In this embodiment, optical sensors are employed and they function as an optical mouse. The direction sensor 71 emits light to the surface of the spheroid 2 and receives the reflective light from the surface of the spheroid 2 through an optical sensor for data record and image comparison, thereby the rotational angle and distance of the spheroid 2 can be obtained.

Figure 4:
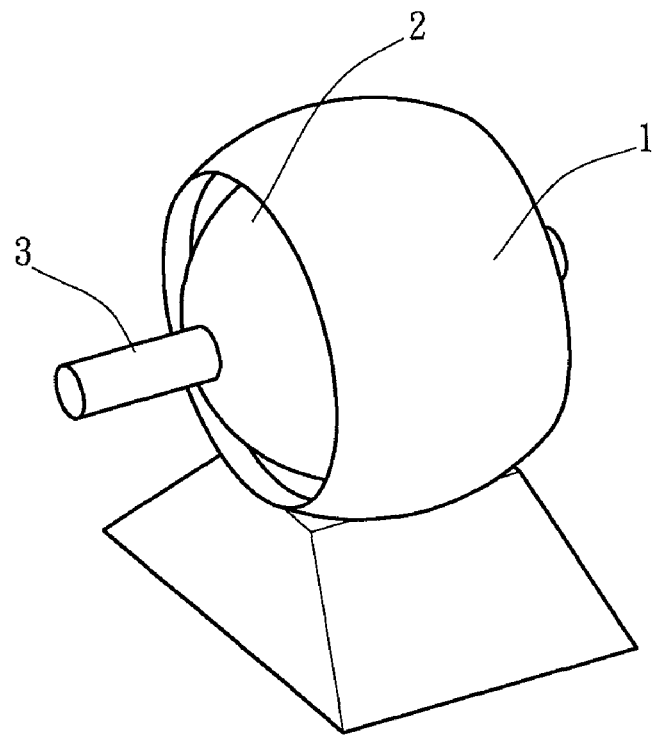
FIG. 4 is a perspective view of the main body according to FIG. 1.
Figure 5:
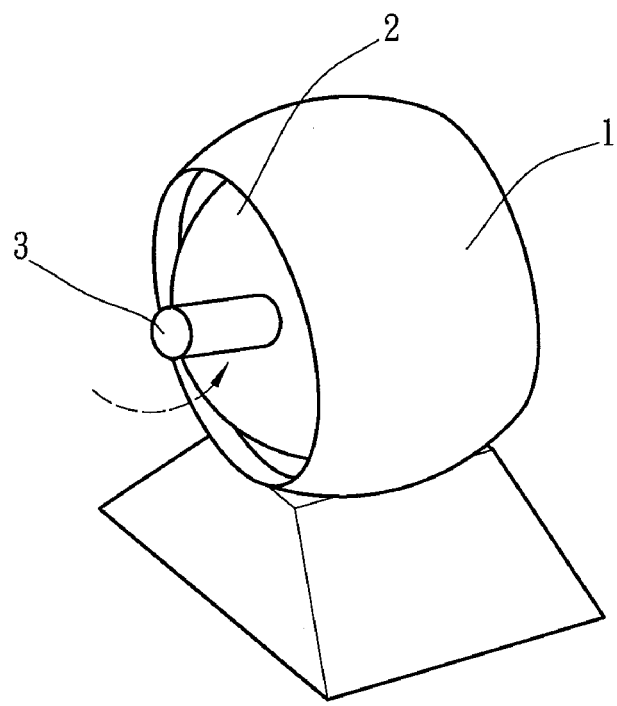
FIG. 5 is a schematic view according to FIG. 4 in a use condition.
Figure 6:
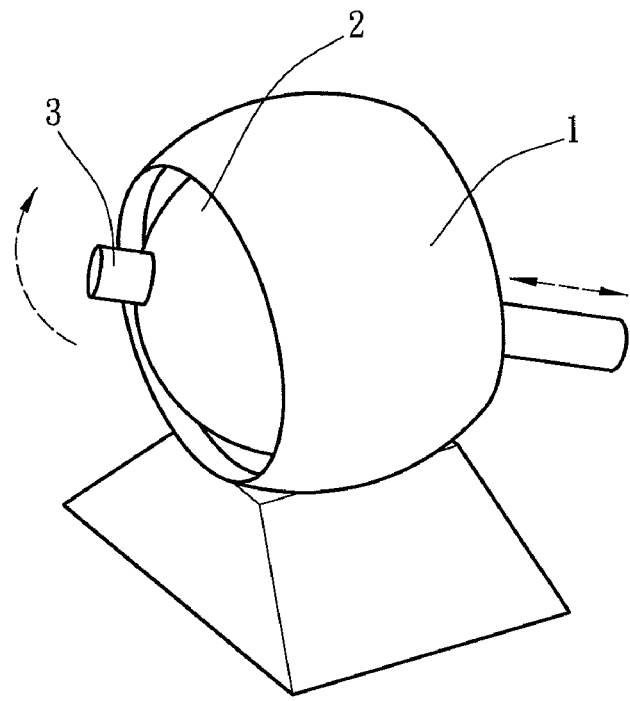
FIG. 6 is a schematic view according to FIG. 4 in another use condition.

Refer to FIGS. 4, 5 and 6 for the invention in use conditions. Through the handle 4 (not shown in the drawings) at one end of the controlling bar 3, the rotation of the spheroid 2 can be controlled in the bracing rack 1. Because of the structure of the spheroid 2 and the arrangement and configuration of the rotational bracing decks, sufficient angles can be provided while simulating rotation of the endoscope to imitate real surgical equipment. Referring to FIG. 5, the controlling bar 3 can be inserted and withdrawn in the spheroid 2 at a depth to meet insertion requirement of the endoscope during actual surgery. Referring to FIG. 6, the controlling bar 3 can be formed in hexagon or polygons to drive the spheroid to turn clockwise or counterclockwise.

By means of the construction set forth above, the apparatus of the invention can provide improved simulation. The apparatus of the invention is simply structured, well designed, easier to use, lower cost, offers higher stability and can be fabricated in a mass production, thus is desirable for teaching, learning and practice.

Figure 7A:
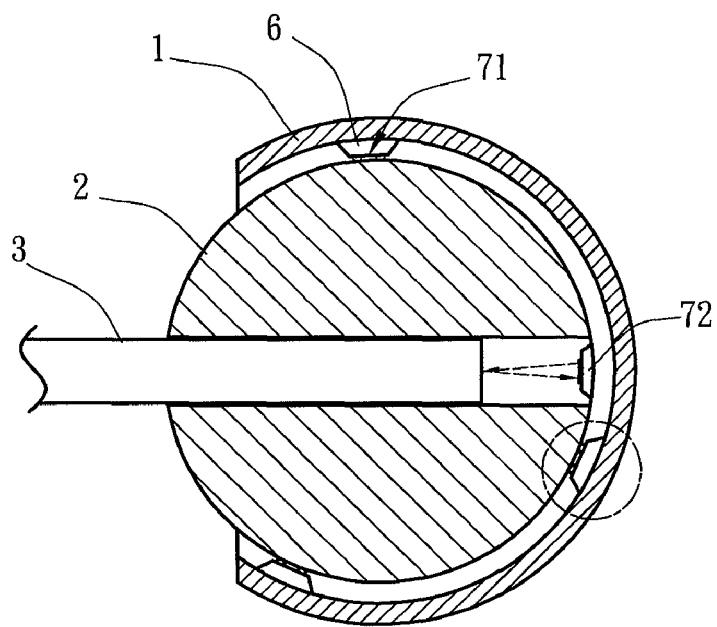
FIG. 7A is a longitudinal cross section of the main body of the second embodiment.
Figure 7B:
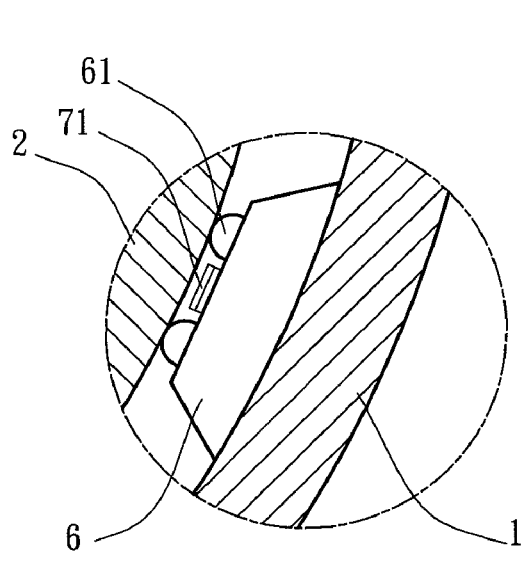
FIG. 7B is an enlarged view in FIG. 7A.
Figure 8:
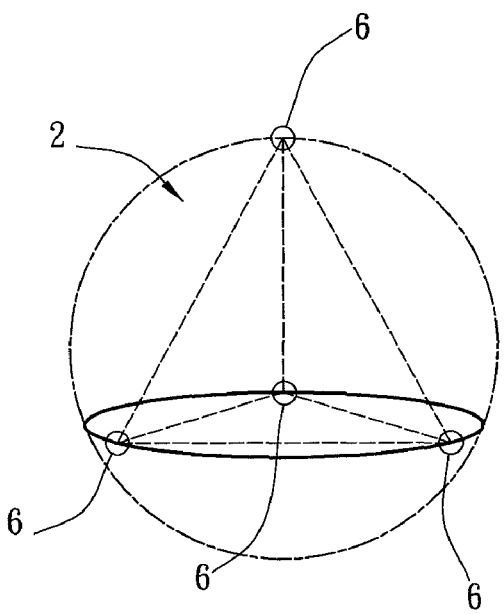
FIG. 8 is a schematic view of the second embodiment showing the positional relationship between the rotational bracing deck and the spheroid.

Embodiment 2:

Referring to FIG. 7A and also FIG. 1, the endoscope simulation apparatus in this embodiment includes a bracing rack 1, a spheroid 2 held in the bracing rack 1 and turnable freely, and a controlling bar 3 running through a passage formed in the middle of the spheroid 2. The passage and controlling bar 3 are formed at a cross section of a regular hexagon. The bracing rack 1 in this embodiment is formed in a semi-closed structure which differs from the embodiment 1. The inner side of the bracing rack 1 and the spheroid 2 are interposed by four rotational bracing decks 6 spaced from one another in a regular tetrahedron. The gravity center of the regular tetrahedron is overlapped with the center of the spheroid 2 as shown in FIG. 8. Such a structure greatly improves the stability of the apparatus, and also provides sufficient movement space for the controlling bar 3. As the semi-closed structure is adopted, the front end of the passage of the spheroid 2 is sealed as shown in the drawings. The depth sensor 72 is an optical distance sensor installed at the front end of the passage opposing the front end of the controlling bar 3. To enhance integration of the structure, the direction sensors 71 in the embodiment are installed at the top portions of the rotational bracing decks 6 as shown in FIG. 7B.

Figure 9A:
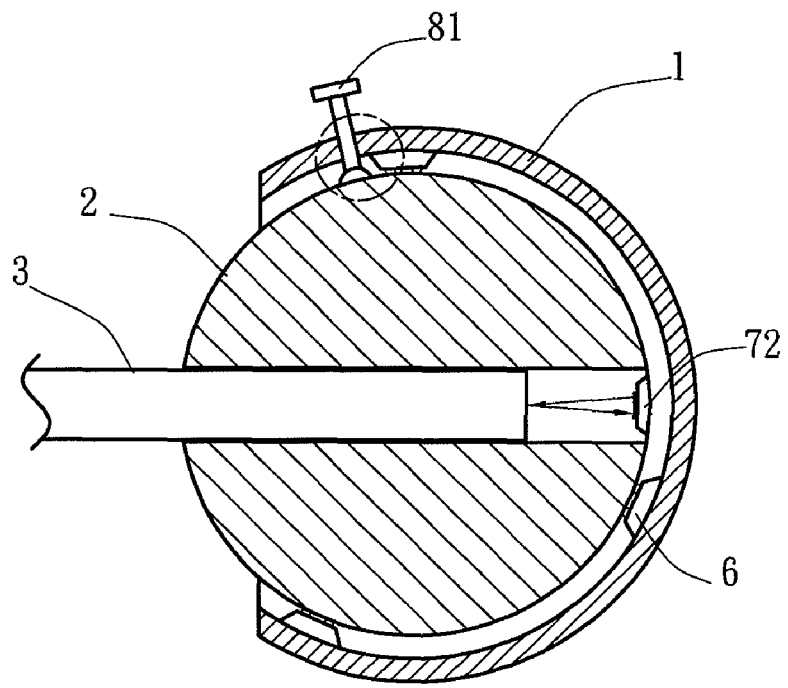
FIG. 9A is a longitudinal cross section of the main body of the third embodiment.
Figure 9B:
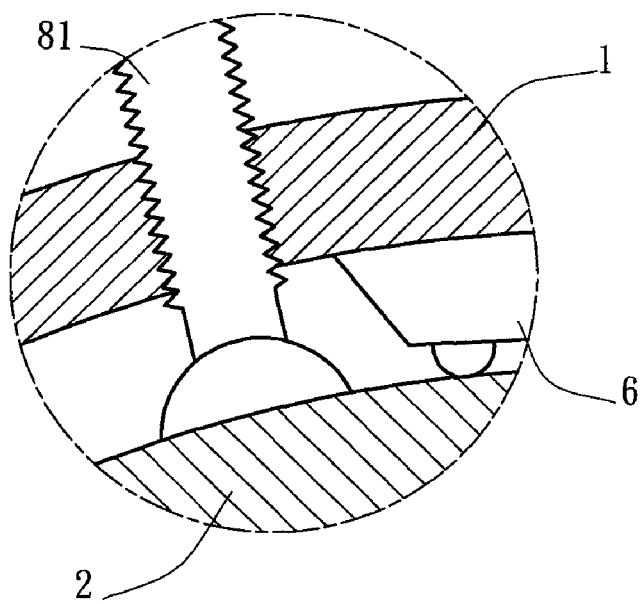
FIG. 9B is an enlarged view in FIG. 9A.
Figure 10:
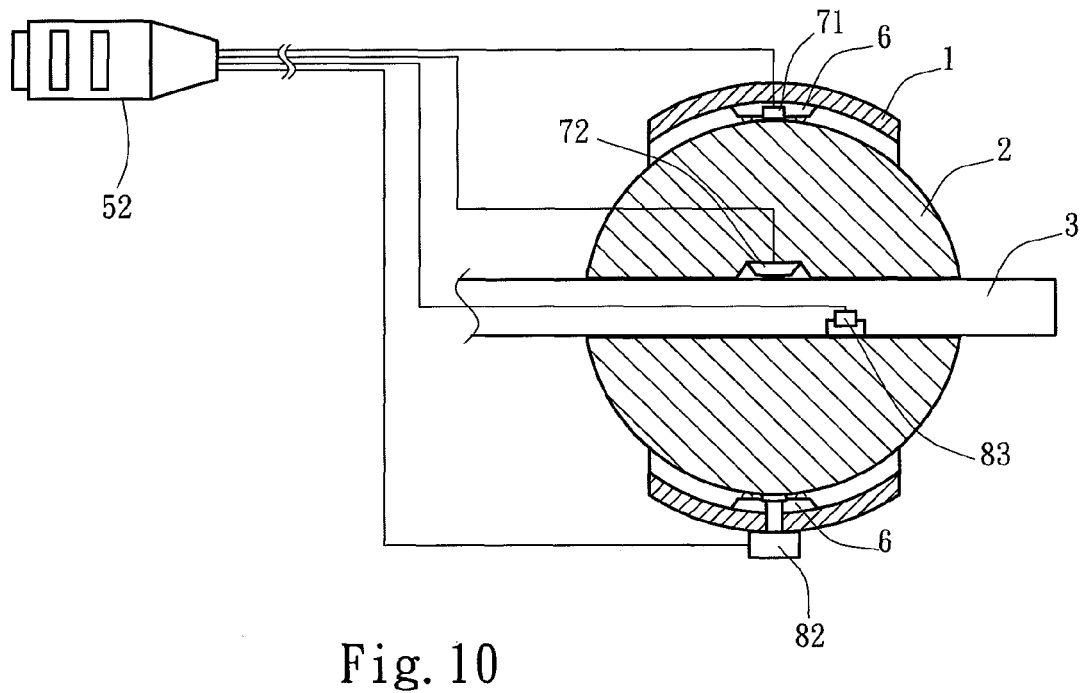
FIG. 10 is a schematic view of the structure of the forth embodiment.
Figure 11:
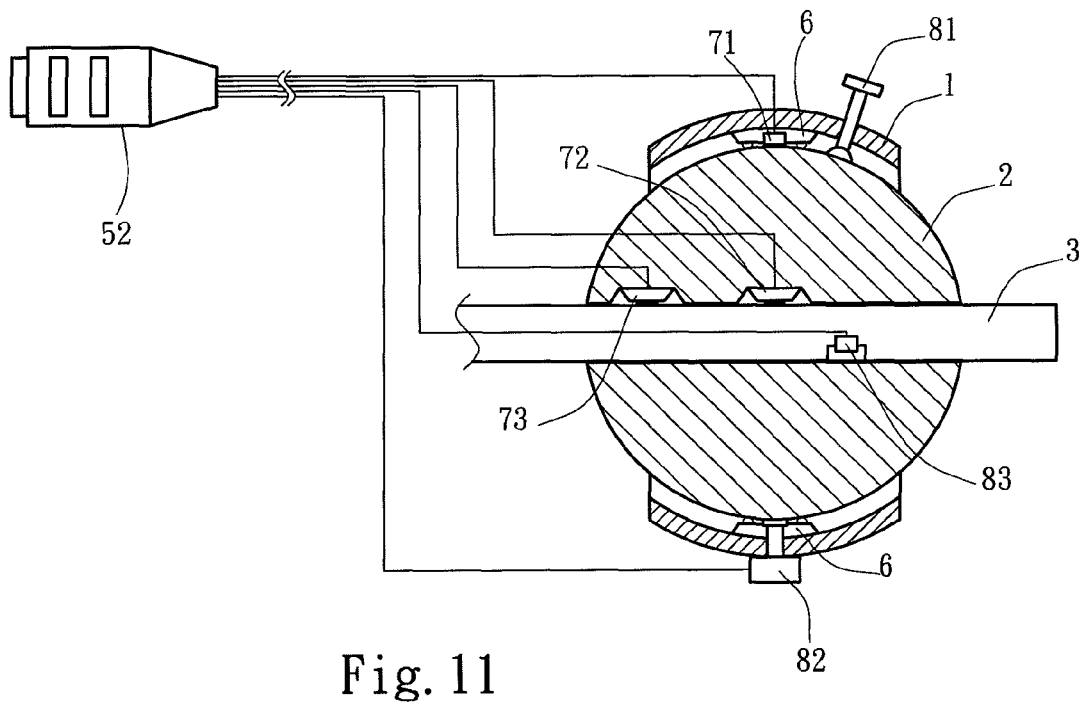
FIG. 11 is a schematic view of the structure of the fifth embodiment.

Embodiment 3:

This embodiment is an improvement of the embodiment 2 previously discussed, with an extra manual damper means 81 abutting the rotational bracing deck 6 as shown in FIG. 9A. Since different portions in a human body form different resistance to the endoscope, users can adjust rotational resistance of the spheroid 2 based on usual practice experiences or skilled doctors based on their experiences to practice strength control during using the endoscope. In this embodiment, the manual damper means 81 includes a handle, bolt and a damper to adjust damping force through turning of the bolt against the bracing rack 1 as shown in FIG. 9B.

Embodiment 4:

This embodiment is a further refinement formed by incorporating the advantages of the previous embodiments. It adopts a semi-closed bracing rack 1 and three rotational bracing racks 6 like the embodiment 1, with the depth sensor 72 held in the spheroid 2 between the passage and the controlling bar 3. It also has two direction sensors 71 installed on the top portions of the rotational bracing decks 6, and a passage and controlling bar 3 formed at a cross section of a regular hexagon like the embodiment 2. Such a structure provides sufficient simulation angular space to imitate rotation of the endoscope and desired stability. There is a feedback automatic adjustment damper means 82 installed on the third rotational bracing deck 6 that has a feedback automatic adjustment device driven electrically to receive control information sent by the computer to adjust rotation damping. There is another feedback automatic adjustment damper means 83 installed between the controlling bar 3 and the spheroid 2 on one side opposing the depth sensor 72 to receive control information from the computer to adjust insertion and withdrawing damping. The direction sensors 71, depth sensor 72, and feedback automatic adjustment damper means 82 and 83 have data lines integrated to connect to the computer through an USB interface 52. Adopted the feedback automatic adjustment damper means provides the benefit of limiting the simulated rotation and insertion and withdrawing of the endoscope based on driving of the simulation software in the computer, thereby can achieve real simulation of moving the endoscope in a human body and encountered resistance. This provides great training aid to foster surgical tactile feel for doctors.

Embodiment 5:

This embodiment is a further improvement based on the embodiment 4 previously discussed. It includes an additional manual damper means 81 like the embodiment 3, and a turning angle sensor 73 between the controlling bar 3 and the spheroid 2. The passage and controlling bar 3 are formed at a circular cross section. The direction sensors 71, depth sensor 72, turning angle sensor 73, and feedback automatic adjustment damper means 82 and 83 have data lines integrated to connect to the computer through an USB interface 52. The turning angle sensor 73 can feed back turning angles of the controlling bar 3 during simulation process to the computer. It is applicable to simulation practice of some special endoscopes, or other surgical equipment, especially asymmetrical electric surgical scalpels and shears and the like.

As a conclusion, the structures provided by the invention are not limited to the embodiments set forth above. The apparatus of the invention is not limited to simulation of the endoscope as single surgical equipment. In practice, two identical simulators can integrate signals through a serial port and send them into the computer to drive the software to process as desired. In such a process two handles of the two simulators can be used cooperatively to practice operation of two hands in a coordinated manner. Other similar structures shall be covered by the scope of the invention.

Figure 12:
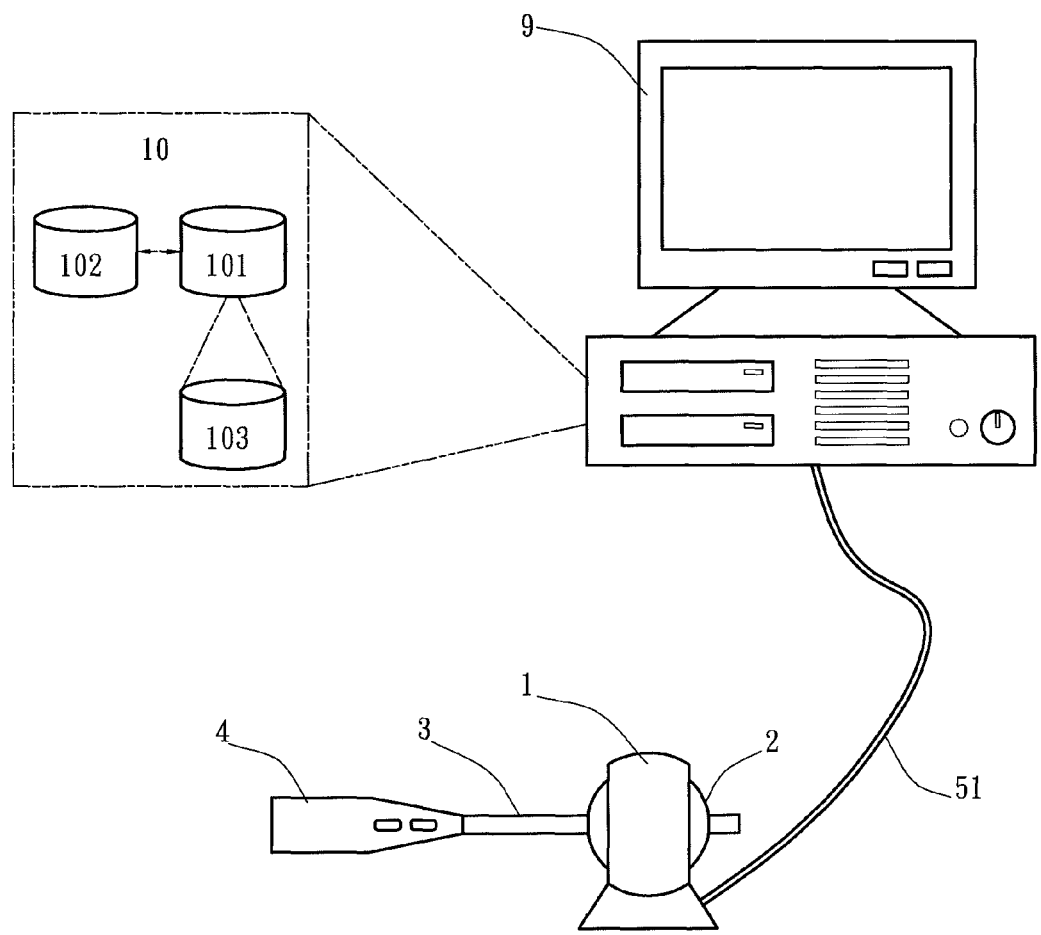
FIG. 12 is a schematic view of the structure of an endoscope simulation system.

Based on the endoscope simulation apparatus previously discussed, the invention further provides an endoscope simulation system as shown in FIG. 12 that includes a computer 9, simulation software 10 installed in the computer 9 and an endoscope simulation apparatus. The computer and endoscope simulation apparatus are connected through a data line 51. The simulation software 10 establishes a human body internal space database 101 and a human body internal image database 102. The human body internal space database 101 has a built-in damping database 103.

Figure 13:
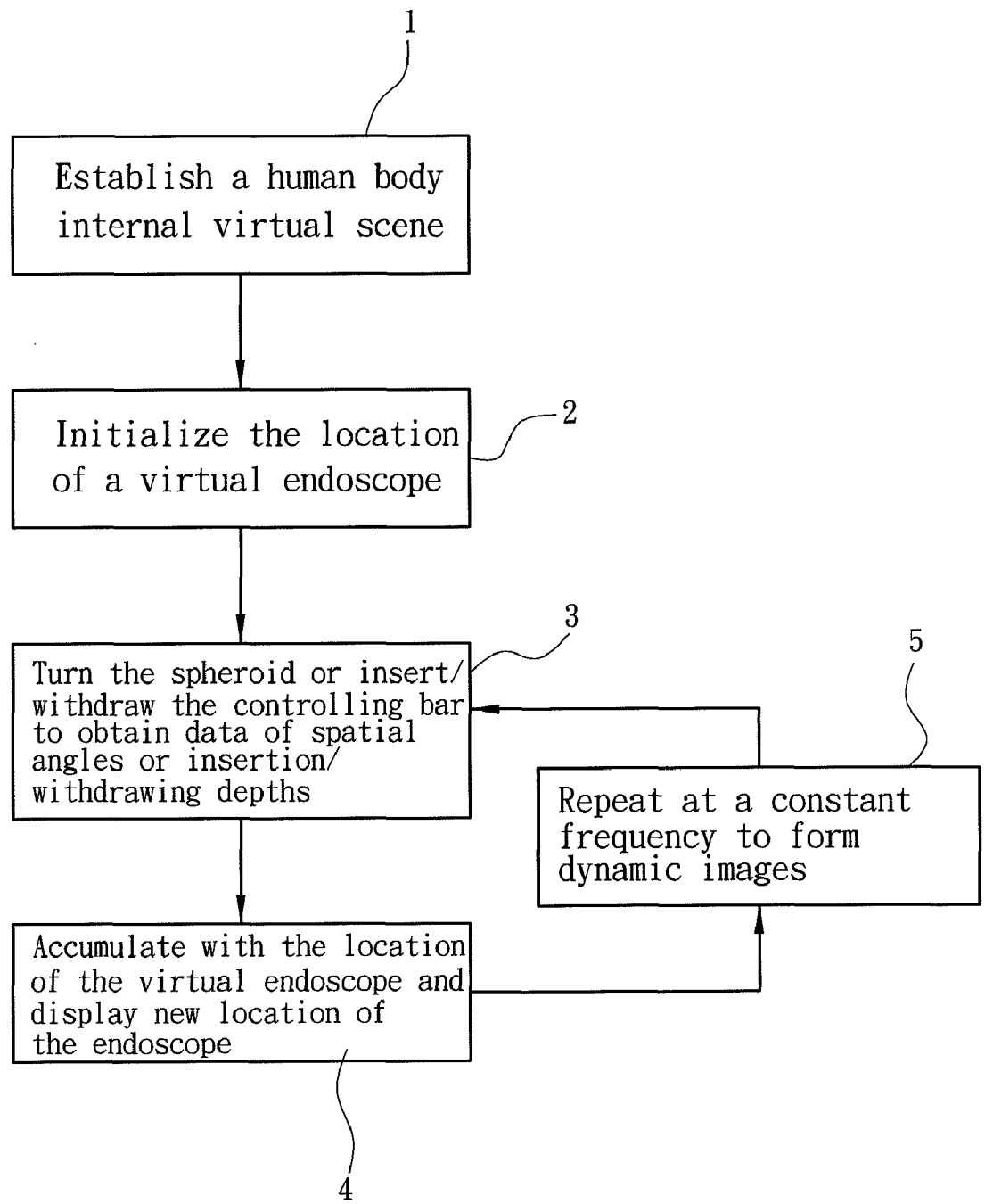
FIG. 13 is a flowchart of a simulation method for simulating movement of an endoscope.

The endoscope simulation system is implemented according to a simulation method that includes the steps as follow, referring to FIG. 13:

1. the computer establishes a human body internal virtual model based on the human body internal space database of the simulation software and incorporates with the human body internal image database to set up a human body internal virtual scene displayed through a display device of the computer;

2. initialize the location of a virtual endoscope and display the location of the virtual endoscope in the virtual scene through the display device;

3. turn the spheroid through the controlling bar or insert and withdraw the controlling bar, and the direction sensors or depth sensor sends data of the rotational spatial angles and insertion/withdrawing depths through the data line to the computer;

4. the simulation software accumulates the data of the rotational spatial angles and insertion/withdrawing depths with the location of the virtual endoscope and displays the location of the virtual endoscope in the virtual scene after moved through the display device; and 5. the direction sensors, depth sensor, simulation software and computer repeat steps 3 and 4 at a constant frequency, and the display device continuously displays different locations of the virtual endoscope in the virtual scene to form continuous dynamic images.

Figure 14:
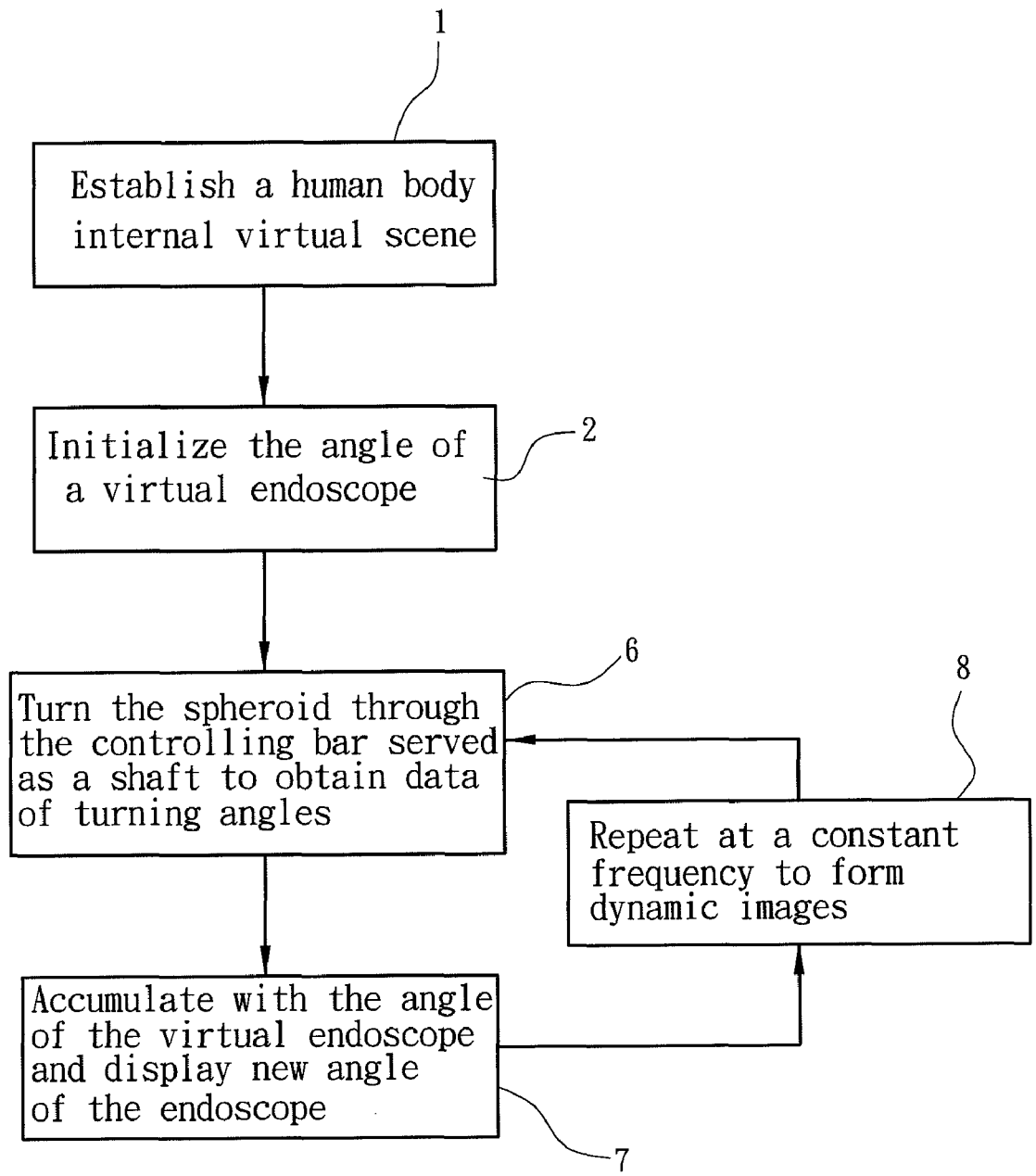
FIG. 14 is a flowchart of the simulation method for simulating rotation of an endoscope.

The simulation method of turning the virtual endoscope is similar to the method of moving previously discussed, and includes the following steps, referring to FIG. 14:

6. the controlling bar is served as a shaft to turn the spheroid, and the direction sensors or turning angle sensor sends angular data of the rotation of the spheroid via the data line to the computer;

7. the simulation software accumulates the angular data with the angle of the virtual endoscope, and displays the location of the virtual endoscope in the virtual scene after rotated through the display device; and 8. the direction sensors, angle sensor, simulation software and computer repeat steps 7 and 8 at a constant frequency, and the display device continuously displays different angles of the virtual endoscope in the virtual scene to form continuous dynamic images.

Figure 15:
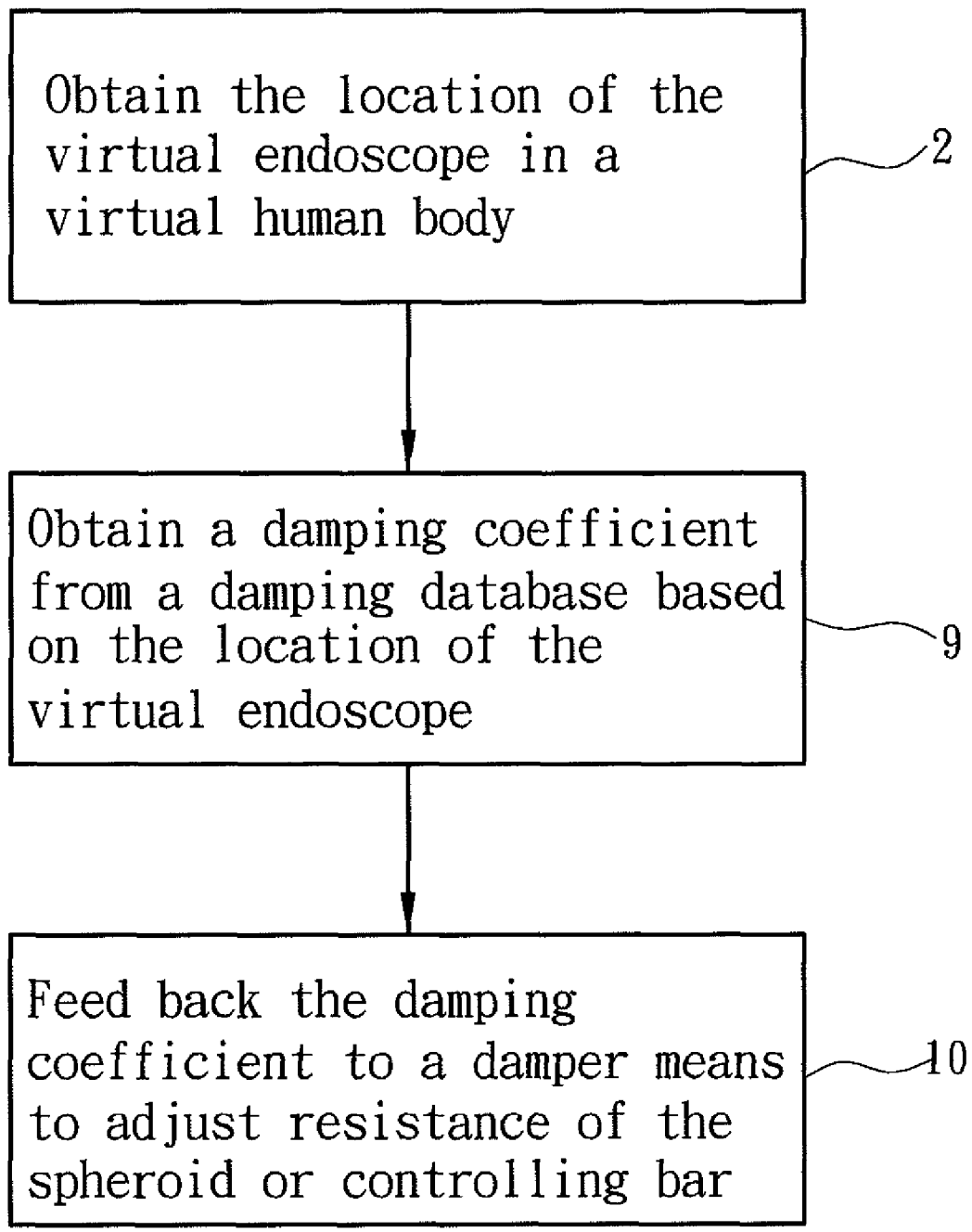
FIG. 15 is a flowchart of the simulation method for simulating endoscope damping.

When the endoscope simulation apparatus is equipped with a feedback automatic adjustment damper means and can perform damping simulation, the damping simulation includes additional steps as follow, referring to FIG. 15:

9. the simulation software obtains rotation and insertion/withdrawing damping coefficients of the virtual endoscope from the damping database based on the location of the virtual endoscope in the virtual scene, and sends to the feedback automatic adjustment damper means; and 10. the feedback automatic adjustment damper means automatically adjusts resistance of rotation and insertion/ withdrawing of the spheroid and the controlling bar based on the damping coefficients.

On locations where the virtual endoscope cannot pass through, such as bones and the like tissues in the human body, the damping coefficient is infinite, then the feedback automatic adjustment damper means brakes the spheroid or controlling bar without moving.

What is claimed is:

1. An endoscope simulation apparatus, comprising a bracing rack, a spheroid and a controlling bar; the spheroid being held in the bracing rack and turnable freely, the controlling bar being slidable relative to the spheroid and installed in a passage running through a center of the spheroid to control rotation of the spheroid, the bracing rack including an inner side spaced from the spheroid to hold at least two direction sensors therebetween, the controlling bar being equipped with a depth sensor.

2. The endoscope simulation apparatus of claim 1, wherein the inner side of the bracing rack and the spheroid are interposed by at least two rotational bracing decks which have respectively a top portion holding rolling balls slidably incorporated with the spheroid.

3. The endoscope simulation apparatus of claim 2, wherein the inner side of the bracing rack and the spheroid are interposed by three rotational bracing decks located respectively on a plane which runs through the center of the spheroid and is spaced evenly from one another relative to the center of the spheroid.

4. The endoscope simulation apparatus of claim 2, wherein the inner side of the bracing rack and the spheroid are interposed by four rotational bracing decks spaced from one another in a regular tetrahedron which has a gravity center overlapped with the center of the spheroid.

5. The endoscope simulation apparatus of claim 2, wherein the passage and the controlling bar are interposed by a turning angle sensor to measure turning angles of the controlling bar relative to the spheroid.

6. The endoscope simulation apparatus of claim 2, wherein the depth sensor is located in the spheroid between the passage and the controlling bar.

7. The endoscope simulation apparatus of claim 2, wherein the depth sensor is located at one end of the passage opposing a distal end of the controlling bar.

8. The endoscope simulation apparatus of claim 6, wherein the direction sensors are abutting the rotational bracing decks.

9. The endoscope simulation apparatus of claim 6, wherein the direction sensors are located on the top portions of the rotational bracing decks.

10. The endoscope simulation apparatus of claim 1, wherein the bracing rack and the spheroid are interposed by a damper means.

11. The endoscope simulation apparatus of claim 1, wherein the spheroid and the controlling bar are interposed by a damper means.

12. The endoscope simulation apparatus of claim 10, wherein the damper means includes a manual adjustment device abutting the rotational bracing decks.

13. The endoscope simulation apparatus of claim 10, wherein the damper means includes a feedback automatic adjustment device located on the top portions of the rotational bracing decks.

14. The endoscope simulation apparatus of claim 1, wherein the controlling bar and the passage are formed respectively in a non-circular cross section.

15. The endoscope simulation apparatus of claim 9, wherein the controlling bar and the passage are formed respectively in a cross section of a regular hexagon.

16. The endoscope simulation apparatus of claim 1, wherein the controlling bar includes a distal end fastened to a simulated endoscope handle and a control button.

17. An endoscope simulation system, comprising a computer, simulation software installed in the computer and an endoscope simulation apparatus, the computer and the endoscope simulation apparatus being connected through a data line, wherein:

the endoscope simulation apparatus includes a bracing rack, a spheroid and a controlling bar, the spheroid being held in the bracing rack and turnable freely, the controlling bar being slidable relative to the spheroid and installed in a passage running through a center of the spheroid to control rotation of the spheroid, the bracing rack including an inner side spaced from the spheroid to hold at least two direction sensors therebetween, the controlling bar being equipped with a depth sensor, the simulation software establishing a human body internal space database and a human body internal image database in the computer.

18. A simulation method applied to the endoscope simulation system of claim 12, comprising the steps of:

a. establishing a human body internal virtual model through the computer based on the human body internal space database of the simulation software and incorporating with the human body internal image database to set up a human body internal virtual scene displayed through a display device of the computer;

b. initializing a location of a virtual endoscope and displaying the location of the virtual endoscope in the virtual scene through the display device;

c. turning the spheroid through the controlling bar or inserting and withdrawing the controlling bar, and sending data of rotational spatial angles and insertion and withdrawing depths through the direction sensors or the depth sensor via a data line to the computer;

d. accumulating the data of the rotational spatial angles and the insertion and withdrawing depths with the location of the virtual endoscope through the simulation software, and displaying the location of the virtual endoscope in the virtual scene after moved through the display device; and e. repeating steps c and d at a constant frequency through the direction sensors, the depth sensor, the simulation software and the computer, and continuously displaying different locations of the virtual endoscope in the virtual scene through the display device to form continuous dynamic images.

19. The simulation method of claim 18 further comprising the steps of:

f. turning the spheroid through the controlling bar served as a shaft, and sending angular data of the rotation of the spheroid through the direction sensors or the turning angle sensor via the data line to the computer;

g. accumulating the angular data with the angle of the virtual endoscope through the simulation software and displaying the location of the virtual endoscope in the virtual scene after rotated through the display device; and h. repeating steps f and g at a constant frequency through the direction sensors, the angle sensor, the simulation software and the computer, and continuously displaying different angles of the virtual endoscope in the virtual scene through the display device to form continuous dynamic images.

20. The simulation method of claim 18, wherein the endoscope simulation apparatus further includes a feedback automatic adjustment damper means and the steps of:
   i. obtaining rotation and insertion/withdrawing damping coefficients of the virtual endoscope from a damping database through the simulation software based on the location of the virtual endoscope in the virtual scene, and sending to the feedback automatic adjustment damper means; and
   j. automatically adjusting resistance of the rotation and insertion and withdrawing of the spheroid and the controlling bar through the feedback automatic adjustment damper means based on the damping coefficients.

* * * * *